US00PP23761P3

(12) United States Plant Patent
LaBonte et al.

(10) Patent No.: US PP23,761 P3
(45) Date of Patent: Jul. 23, 2013

(54) ***SWEETPOTATO* PLANT NAMED '05-111'**

(50) Latin Name: ***Ipomoea batatas* (L.) Lam.**
Varietal Denomination: 05-111

(75) Inventors: Don R. LaBonte, Baton Rouge, LA (US); Arthur Q. Villordon, Monroe, LA (US); Tara Smith, Chase, LA (US); Christopher A. Clark, Baton Rouge, LA (US)

(73) Assignee: Board of Supervisors of Louisiana State University and Agricultural and Mechanical College Through The LSU Agcenter, Baton Rouge, LA (US)

( * ) Notice: Subject to any disclaimer, the term of this patent is extended or adjusted under 35 U.S.C. 154(b) by 0 days.

(21) Appl. No.: 13/373,630

(22) Filed: Nov. 22, 2011

(65) Prior Publication Data

US 2013/0133118 P1 May 23, 2013

(51) Int. Cl.
*A01H 5/00* (2006.01)

(52) U.S. Cl.
USPC ..... Plt./258

(58) Field of Classification Search
USPC ..... Plt./258
See application file for complete search history.

*Primary Examiner* — Annette Para
(74) *Attorney, Agent, or Firm* — James C. Carver

(57) ABSTRACT

A new variety of sweetpotato identified as '05-111' is disclosed having disease resistance to both *Fusarium* wilt, *Rhizopus* soft rot, and *Streptomyces* soil rot, a orange flesh, and high yield characteristics.

3 Drawing Sheets

The development of this invention was partially funded by the Government through a grant for the United States Department of Agriculture, USDA NIFA Grant Number NA/LAB93957. The Government may have certain rights in this invention.

This invention pertains to a new and distinct variety of sweetpotato.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

Genus and Species Name

This new and distinct sweetpotato variety, *Ipomoea batatas* (L.) Lam., demonstrates superior disease resistance to Fusarium wilt, soil rot, and Rhizopus soft rot and exhibits an orange flesh. It also demonstrates high yield characteristics in comparison to 'Beauregard'.

Variety Denomination

This new and distinct sweetpotato variety is identified as '05-111', and is characterized by an orange flesh, high yield, and consistent shape.

BRIEF DESCRIPTION OF THE DRAWINGS

The file of this patent contains at least one photograph executed in color. Copies of this patent or patent application with color drawing(s) will be provided by the Patent and Trademark Office upon request and payment of the necessary fee.

DETAILED BOTANICAL DESCRIPTION

This new variety of sweetpotato, named '05-111', was observed 90-110 days after planting. This new variety of sweetpotato, named '05-111', resulted from an open pollinated cross performed in 1995 to the female parent '97A14' (not patented). The male parent was unknown. Four patented male parents ('L96-117' (U.S. Plant Pat. No. 15,038 P2); 'Bienville' (U.S. Plant Pat. No. 15,380 P3); 'Evangeline' (U.S. Plant Pat. No. 19,710 P3); and 'Murasaki-29' (U.S. Plant Pat. No. 19,955 P2) were among the potential pollen sources in the crossing nursery. '05-111' was developed to provide a variety with characteristics similar to 'Beauregard' (unpatented), but with improved yield and more consistent shape. '05-111' was characterized by an orange flesh.

Plants of '05-111' and 'Beauregard' are difficult to distinguish. A red [5 R (red) P (purple) (4/6)] marking at the base of the leaf junction with the petiole is larger in comparison to a similar marking found on 'Beauregard' and extends for 1-2 cm from the junction in adaxial veins of mature leaves and was present throughout major adaxial veins in immature leaves. 'Beauregard' has no red hue to veins. Color terminology used herein is in accordance with the MUNSELL® Book of Color (Munsell Color, GretagMacbeth LLC, 617 Little Britain Road, New Windsor, N.Y. 12553-6148). The color descriptions and color illustrations are as nearly true as is reasonably possible. However, it is understood that both color and other phenotypic expressions described herein may vary from plant to plant with differences in growth, environment and cultural conditions, without any change in the genotype of the variety '05-111'.

'05-111' roots were stored during the winter at Chase, La. '05-111' was planted the following spring, resulting in approximately 8-10 sprouts per root. Cuttings from the sprouts were transplanted successfully for asexual reproduction. Asexual propagation of the new cultivar by cuttings has shown that the unique features of this new sweetpotato were stable and that the plant reproduced true to type in successive generations of asexual propagation. Plants described herein were approximately 90-110 days in age from planting in full sun field plantings.

Figure 1:
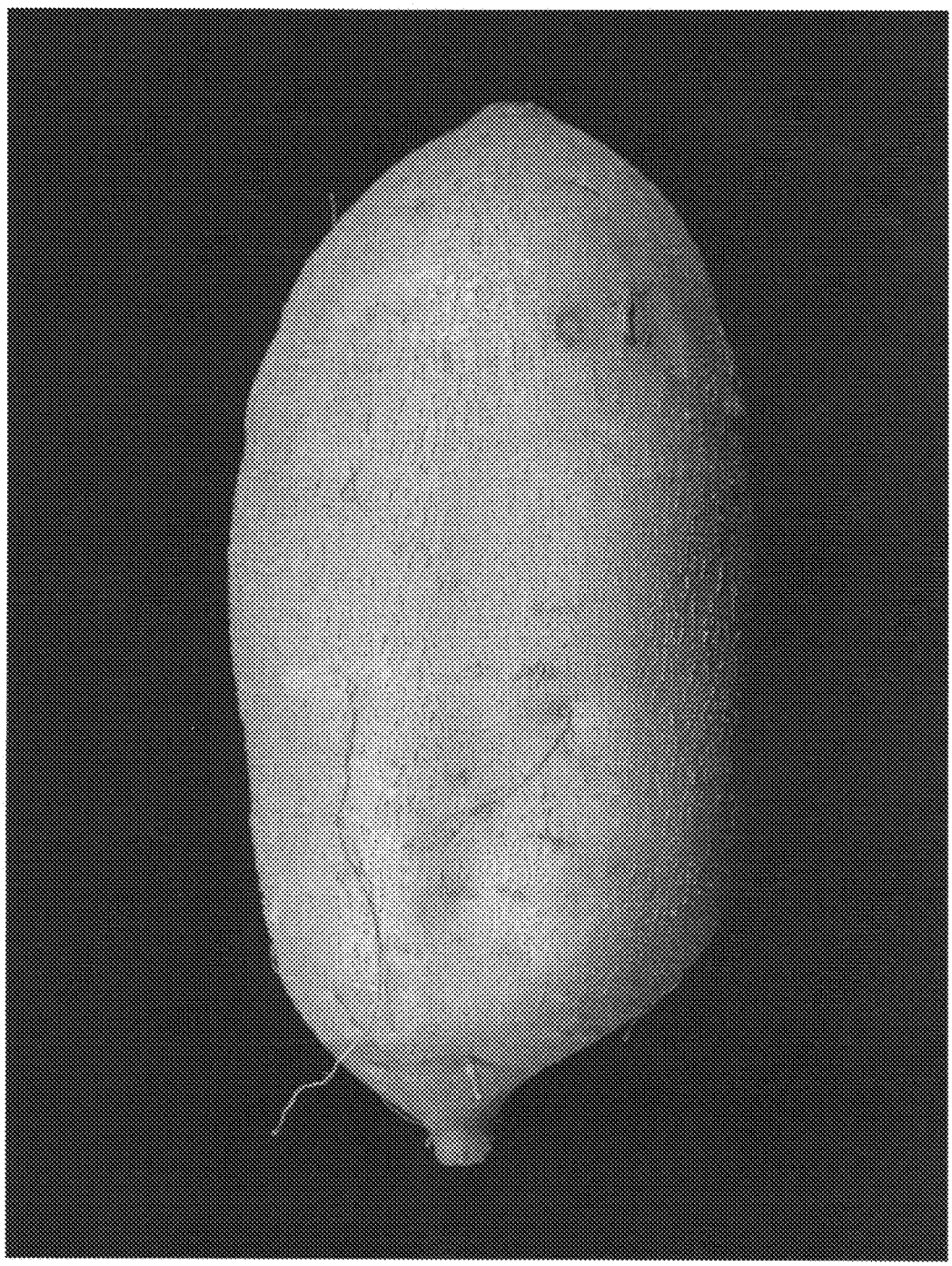
FIG. 1 is a color photograph of the fleshy root form of the novel variety of sweetpotato identified as '05-111'.
Figure 2:
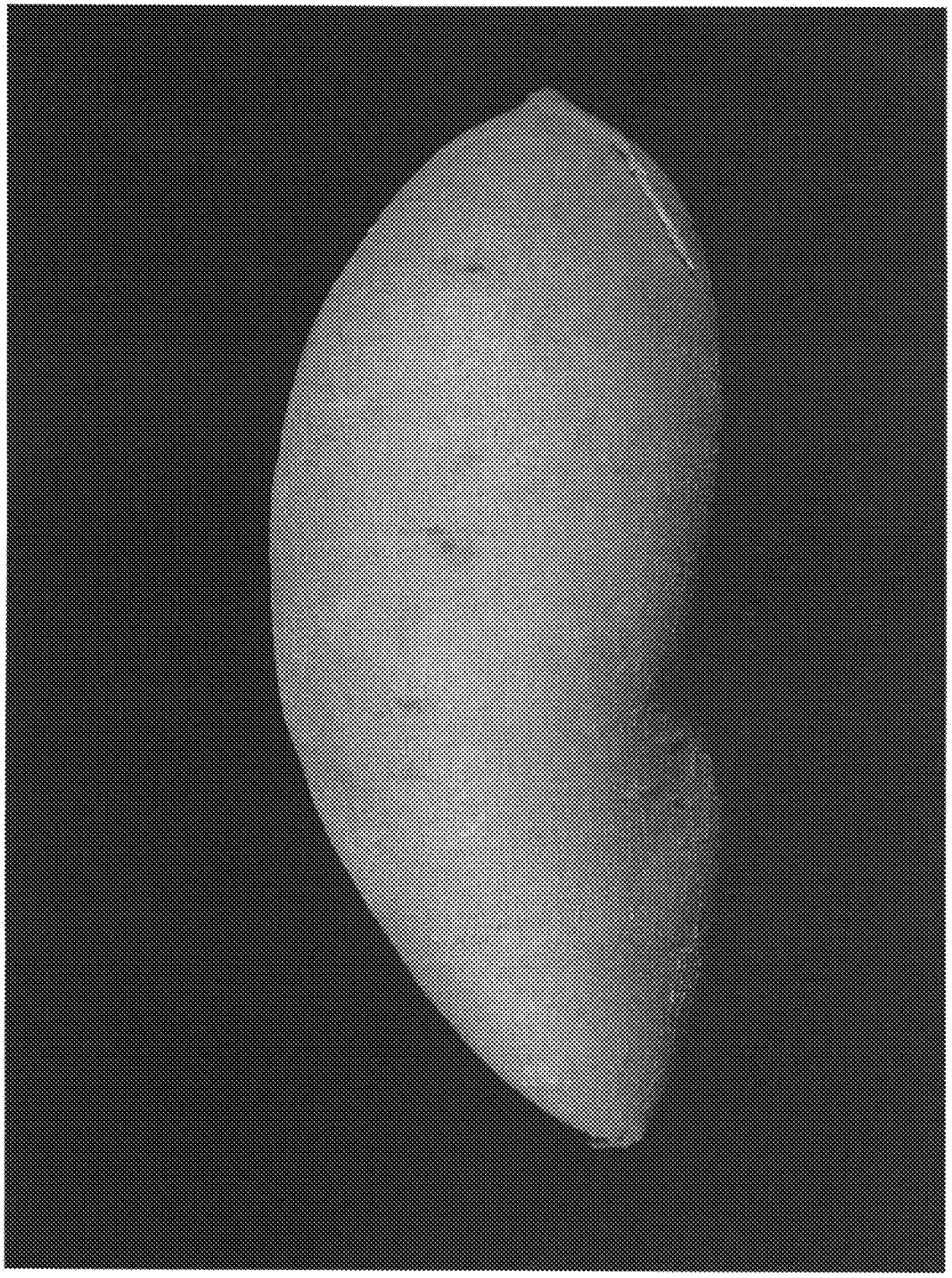
FIG. 2 is a color photograph of the fleshy root form of the sweetpotato variety identified as 'Beauregard'.

FIG. 1 depicts the fleshy root form of the '05-111' sweetpotato. The skins vary from light to medium rose, which is similar to 'Beauregard', both at harvest and after several months of storage as shown in Table 1. MUNSELL® Book of Color values for skin and flesh for both '05-111' and 'Beauregard' storage roots after 6 months of storage are shown in Table 1. The 'Beauregard' sweetpotato is depicted in FIG. 2. The skin for both '05-111' and 'Beauregard' was smooth. '05-111' storage roots were elliptical without lobing, and tend to be slightly longer than 'Beauregard'. The '05-111' cortex was 4 mm in depth and the color similar throughout. The flesh of '05-111' is similar to 'Beauregard'.

TABLE 1

| Variable | Variety | Color |
|---|---|---|
| Skin | '05-111' | 10 R (red) 6/4 |
| | 'Beauregard' | 10 R (red) 6/6 |
| Flesh | '05-111' | 2.5 Y (yellow) R (red) 7/10 |
| | 'Beauregard' | 2.5 Y (yellow) R (red) 7/10 |

Figure 3:
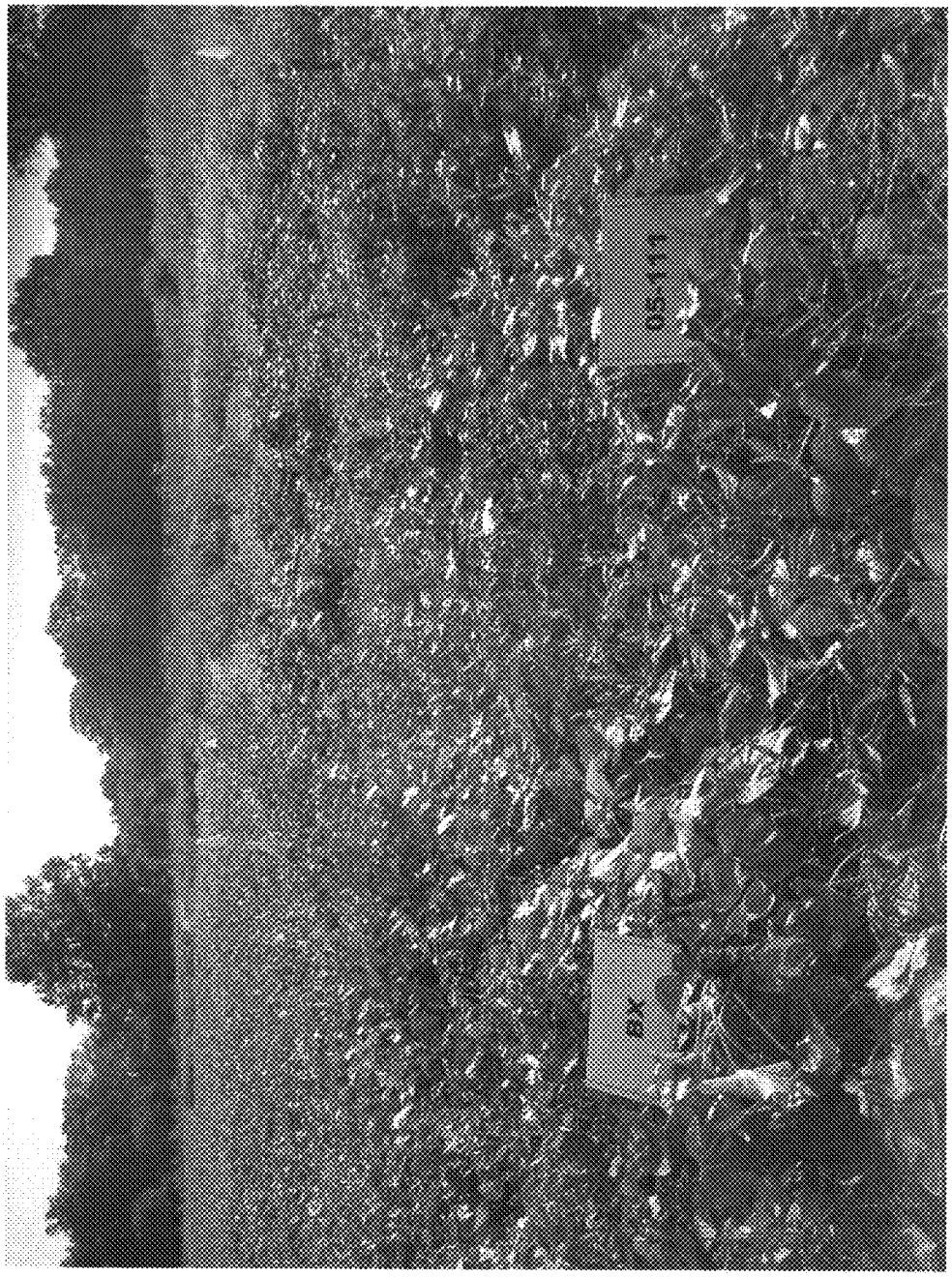
FIG. 3 is a color photograph of the canopy biomasses of the variety of sweetpotato identified as 'Beauregard' (shown on the left side of the photograph) and the novel variety identified as '05-111' (shown on the right side of the photograph).

FIG. 3 depicts the canopy biomass of both '05-111' sweetpotatoes and 'Beauregard' sweetpotatoes. '05-111' has green-stemmed vines [2.5 G (green) Y (yellow) (6/8)] from the apex to the crown of the roots. The '05-111' canopy biomass appears similar to 'Beauregard'. The '05-111' canopy architecture was 22 cm in height from the soil surface and 305 cm in a radial spread. For '05-111', three to four main vines arose from the main stem near the soil surface. The stem giving rise to these vines was 2.0-2.5 cm in diameter; the 3-4 lateral vines were 213 cm in length with diameters of about 0.5-0.6 cm at 65 cm from the base, diameters of about 0.7 cm at the base of the vine, and diameters of about 0.6 cm at the first internode of the first fully developed leaf from the apex. Five to seven lateral branches arose from each of the main vines. At the first internode from the apex, the internode length was about 3.9 cm between the first and second fully developed leaves. Internode lengths for other sections of the vine averaged about 4.9 cm. Unfolded immature leaves were dark green [2.5 G (green) Y (yellow) (3/4)] for the upper and green for the lower surface [2.5 G (green) Y (yellow) (4/4)], which change gradually over one to two nodes from the apex to a green upper surface [5 G (green) Y (yellow) (4/4)] to a green lower surface [5 G (green) Y (yellow) (3/4)]. Mature leaves at five nodes from the apex had an acute apex and mostly a cordate base and a smooth leaf margin. Mature leaves were about 11.7 cm long and 13.3 cm wide. Abaxial and adaxial veins were green [7.5 G (green) Y (yellow) (7/4)]. The petiole was green [2.5 G (green) Y (yellow) (4/4)] and similar to the leaf lamina. A red [5 R (red) P (purple) (4/6)] marking was at the base of the leaf junction with the petiole. This coloration is faded but present in major adaxial veins in immature leaves, while diminished in mature leaves, extending for only 1-2 cm from the junction. The petiole was 12 cm long at five nodes from the apex, and 3-4 mm in diameter at 5 cm from the leaf junction. The dormant nodal meristem also was green [5 G (green) Y (yellow) (4/6)].

A typical inflorescence of '05-111' displayed two to four clusters of three to six flowers per peduncle. Peduncles were green [2.5 G (green) Y (yellow) (5/8)], about 10-14 cm long, and about 4 mm in diameter. Individual flowers were about 4.5 cm long from the base of the calyx, and the corolla was 3.5 to 4 cm wide at the opening. The fused flower petals formed a pentagonal pattern with smooth edges. The inner throat of the corolla appeared purple [2.5 R (red) P (purple) (3/6)]. The inner and outer limbs of the corolla (corollas outermost area, distal from the calyx) were very light purple [2.5 R (red) P (purple) (7/6)]. The five sepals comprising the calyx were elliptic with a cordate apex and appeared to be green [2.5 G (green) Y (yellow) (5/2)]; three of these sepals were about 10 mm long and 4 mm wide. Two other sepals (interspersed) were about 7 mm long and 2 mm wide. Sepal margins were smooth. Stigmata were about 1.7 cm long and appeared to be purple [2.5 R (red) P (purple) (7/6)]. Four of the five stamens were inferior to stigmata. A slight fragrance was present.

EXAMPLE 1

Tests Conducted

To confirm that '05-111' was a new variety, controlled tests (e.g., pathogen responses and yield) were conducted at Baton Rouge, La. 'Beauregard' was selected for comparison because of its importance in commercial United States orange flesh sweetpotato acreage. Diseases that commonly affect the growth of sweetpotatoes were selected to test for pathogen responses in both varieties. Scions of '05-111' and 'Beauregard' reacted similarly to most diseases evaluated in the controlled tests. '05-111' and 'Beauregard' were intermediate to resistant for *Streptomyces* soil rot caused by *Streptomyces ipomoeae* (Person & W. J. Martin) Waksman & Henrici. '05-111' and 'Beauregard' were resistant to *Fusarium* wilt or stem rot caused by *Fusarium oxysporum* Schlect. f. sp. batatas (Wollenw.) Snyd. & Hans.

Nematode reproduction was measured in greenhouse tests. '05-111' and 'Beauregard' were susceptible to southern root-knot nematode, *Meloidogyne incognita* (Kofoid & White 1919) Chitwood 1949. '05-111' and 'Beauregard' were resistant to *Rhizopus* soft rot caused by *Rhizopus stolonifer* (Elm ex. Fr.) Lind. '05-111' and 'Beauregard' were susceptible to bacterial root rot caused by *Dickeya dadantii* Samson et al. as measured by postharvest inoculation of storage roots.

'05-111' did not appear to show any novel insect resistance.

To determine yield production, complete-block trials using four replications of '05-111' and 'Beauregard' each were conducted in 2008 and 2009 in areas of Louisiana, Miss., and Alabama likely to produce '05-111'. '05-111' and 'Beauregard' sweetpotato plants were transplanted in randomized complete-block trials at 31 cm spacings. Each block/plot was fertilized with approximately 250 pounds per acre of a mixed fertilizer comprising 13% N, 13% $P_2O_5$, and 13% $K_2O$. '05-111' was compared to 'Beauregard' at transplanting dates beginning in May-July. Average yields were measured for the following grades of roots: U.S. #1 (51-89 mm in diameter, 76-229 mm long); Canner (25-51 mm in diameter, 51-178 mm long); and Jumbo (larger than U.S. #1 in diameter, length or both, and without objectionable defects). A typical marketable root of '05-111' was 180-190 mm long, 60-70 mm in diameter, with mostly round-elliptic in shapes. The base or distal end tended to be more elongated in comparison to slightly rounder apex (proximal end). U.S. #1 roots typically weighed 150-190 g.

A mid-season transplanting date trial was conducted at Grand Prairie, La. in 2009. '05-111' and 'Beauregard' were transplanted on May 27, 2009, and harvested on Sep. 30, 2009 (126 days after planting). Average yields, measured as Metric Tons per Hectare ($MT \cdot ha^{-1}$), are shown in Table 2.

TABLE 2

| Selection | US#1† | Canners† | Jumbos† | TMY‡† |
|---|---|---|---|---|
| '05-111' | 33.59a | 7.02a | 1.05a | 41.65a |
| 'Beauregard' | 32.86a | 6.10a | 4.36a | 43.32a |

†Average yields in $MT \cdot ha^{-1}$ of varieties followed by a common letter do not differ significantly ($P < 0.05$) according to Duncan's Multiple Range Test.
TMY‡ = total marketable yield An early-season transplanting date trial was also conducted at Foley, Ala. on May 2, 2009, and harvested on Sep. 21, 2009 (123 days after planting). Average yields ($MT \cdot ha^{-1}$) by grade of '05-111' and 'Beauregard' are shown in Table 3.

TABLE 3

| Selection | US#1† | Canners† | Jumbos† | TMY‡† |
|---|---|---|---|---|
| '05-111' | 25.27a | 12.44a | 1.71a | 39.42a |
| 'Beauregard' | 26.60a | 9.27a | 0b | 38.81b |

†Average yields in $MT \cdot ha^{-1}$ of varieties followed by a common letter do not differ significantly ($P < 0.05$) according to Duncan's Multiple Range Test.
TMY‡ = total marketable yield A mid-season transplanting date trial was also conducted at Vardaman, Miss. on Jun. 3, 2009, and harvested on Oct. 1, 2009 (120 days after planting). Average yields ($MT \cdot ha^{-1}$) by grade of '05-111' and 'Beauregard' are shown in Table 4.

TABLE 4

| Selection | US#1† | Canners† | Jumbos† | TMY‡† |
|---|---|---|---|---|
| '05-111' | 22.36a | 13.39a | .90a | 41.29a |
| 'Beauregard' | 15.97a | 22.75a | 3.10a | 43.03a |

†Average yields in $MT \cdot ha^{-1}$ of varieties followed by a common letter do not differ significantly ($P < 0.05$) according to Duncan's Multiple Range Test.
TMY‡ = total marketable yield A late-season transplanting date trial was also conducted at Grand Prairie, La. on Jul. 2 , 2008, and harvested on Nov. 11, 2008 (132 days after planting). Average yields ($MT \cdot ha^{-1}$) by grade of '05-111' and 'Beauregard' are shown in Table 5.

TABLE 5

| Selection | US#1† | Canners† | Jumbos† | TMY‡† |
|---|---|---|---|---|
| '05-111' | 24.09a | 9.75a | 1.51a | 35.36a |
| 'Beauregard' | 13.62a | 7.06a | 3.64a | 24.32a |

†Average yields in $MT \cdot ha^{-1}$ of varieties followed by a common letter do not differ significantly ($P < 0.05$) according to Duncan's Multiple Range Test.
TMY‡ = total marketable yield A mid-season transplanting date trial was also conducted at Wisner, La. on May 27, 2009, and harvested on Nov. 5, 2009 (162 days after planting). Average yields ($MT \cdot ha^{-1}$) by grade of '05-111' and 'Beauregard' are shown in Table 6.

TABLE 6

| Selection | US#1† | Canners† | Jumbos† | TMY‡† |
|---|---|---|---|---|
| '05-111' | 35.52a | 8.37a | 4.88a | 48.82a |
| 'Beauregard' | 32.72a | 10.92a | 3.42a | 50.91a |

†Average yields in $MT \cdot ha^{-1}$ of varieties followed by a common letter do not differ significantly ($P < 0.05$) according to Duncan's Multiple Range Test.
TMY‡ = total marketable yield As shown in Tables 2-6, '05-111' produced yields comparable to, and exceeding 'Beauregard' in regional trials at various planting dates. Yield in comparison to 'Beauregard' in heavier silt loam soils (Tables 2, 5, and 6) were similar to outcomes in lighter, sandy loam soils (Tables 3 and 4). Replicated plots at other farms and on station have shown '05-111' has consistent yields for early, middle, or late season plantings. Yield declines are within norms in poor environments. '05-111' had harvestable roots approximately 115-120 days after planting, which is typical development time for sweetpotatoes and comparable to 'Beauregard'. The yield of Jumbo grade is indicative of earliness and '05-111' was similar to the jumbo yield of 'Beauregard' statistically; however, rank changed from plot to plot. Yield in 5 other plots (data not shown) in Louisiana in years 2007 and 2008 showed no significant difference in yield in comparison to the 'Beauregard' variety for the important U.S. #1 grade. Yield of '05-111' for U.S. #1 grade was significantly higher in one plot in 2007 in comparison to 'Beauregard'. In total, '05-111' ranked higher in yield of U.S. #1 grade in 14 out of 19 farm plots in comparison to 'Beauregard' (years 2007-2010). '05-111' was also trialed at Chase, La. in 2006. '05-111' did not differ in yield in comparison to 'Beauregard' in an early planting; however, a late planting of '05-111' was significantly higher in yield in comparison to 'Beauregard'. Gross yield of U.S. #1 grade was highest when estimates were made from flood damaged fields (Tables 4 and 5), suggesting that '05-111' has more tolerance to saturated soil conditions in comparison to 'Beauregard'; however, additional data are needed to substantiate flooding tolerance. In total, this data reflects consistent high yield characteristics for '05-111'.

Sugar profiles for baked '05-111' and 'Beauregard' are shown in Table 7. For this 2009 test, roots were stored for five months after which they were baked at 190° C. for approximately 2.0 h. Sucrose and maltose content in baked '05-111' was similar to that found in baked 'Beauregard'. Total sugar content was also similar. Dry matter is similar for '05-111' (20.8%) and 'Beauregard' (21.0%). These results demonstrate a similar level of sweetness and moistness for '05-111' and 'Beauregard'.

TABLE 7

| Selection | Fructose‡ | Glucose‡ | Sucrose‡ | Maltose‡ | Total sugars†‡ |
|---|---|---|---|---|---|
| '05-111' | 1.16 | 1.62 | 2.78 | 5.79 | 11.35 |
| 'Beauregard' | 1.10 | 1.51 | 2.91 | 6.02 | 11.54 |

†Total sugars = fructose + glucose + maltose + sucrose.
‡$mg \cdot g^{-1}$ fresh weight basis.

'05-111' should be a valuable commercial sweetpotato variety. '05-111' produced plants (sprouts) comparable to 'Beauregard'. Days to harvest for '05-111' were similar to 'Beauregard'. '05-111' exhibited similar sugar profiles in comparison to 'Beauregard'. '05-111' has exhibited superior yield in late plantings in comparison to 'Beauregard', when unfavorably wet conditions were present.

We claim:

1. A new and distinct variety of *Ipomoea batatas* plant named '05-111' as described and illustrated in the specification herein.

* * * * *